United States Patent [19]
Benson et al.

[11] Patent Number: 5,916,661
[45] Date of Patent: *Jun. 29, 1999

[54] SELECTIVELY APERTURED NONWOVEN WEB

[75] Inventors: Douglas H. Benson, West Harrison, Ind.; John J. Curro, Cincinnati, Ohio

[73] Assignee: The Procter & Gamble Company, Cincinnati, Ohio

[ * ] Notice:

[ * ] Notice: This patent is subject to a terminal disclaimer.

[21] Appl. No.: 08/810,205

[22] Filed: Mar. 3, 1997

Related U.S. Application Data

[63] Continuation of application No. 08/536,228, Sep. 29, 1995, Pat. No. 5,628,097.

[51] Int. Cl.[6] .............................. B32B 3/24; A61F 13/46
[52] U.S. Cl. ......................... 428/131; 428/138; 428/198; 604/378; 604/383
[58] Field of Search .................................. 428/131, 138, 428/198; 604/378, 383

[56] References Cited

U.S. PATENT DOCUMENTS

| | | | |
|---|---|---|---|
| 3,459,618 | 8/1969 | Egler | 156/219 |
| 4,333,979 | 6/1982 | Sciaraffa et al. | 428/179 |
| 4,588,630 | 5/1986 | Shimalla | 428/131 |
| 5,567,501 | 10/1996 | Srinivasan et al. | 428/131 |
| 5,628,097 | 5/1997 | Benson et al. | 28/165 |
| 5,658,639 | 8/1997 | Curro et al. | 28/165 |

FOREIGN PATENT DOCUMENTS

| | | | |
|---|---|---|---|
| 0 360 472 | 3/1990 | European Pat. Off. | A61F 13/15 |
| 0 403 187 | 12/1990 | European Pat. Off. | B32B 5/18 |
| 0 598 970 A1 | 6/1994 | European Pat. Off. | B26F 1/24 |
| 2175026 | 11/1986 | United Kingdom . | |
| 2 279 878 | 1/1995 | United Kingdom | A61F 13/15 |

*Primary Examiner*—William P. Watkins III
*Attorney, Agent, or Firm*—Edward J. Milbrada; E Kelly Liman; Jacobus C. Rasser

[57] ABSTRACT

The present invention provides a method for selectively aperturing a nonwoven web. A nonwoven web is weakened along a plurality of locations and then a tensioning force is applied to the nonwoven web causing the nonwoven web to rupture at the plurality of weakened location creating a plurality of apertures in the nonwoven web coincident with the weakened locations

13 Claims, 7 Drawing Sheets

SELECTIVELY APERTURED NONWOVEN WEB

This is a continuation of application Ser. No. 08/536,228, filed on Sep. 29 1995, U.S. Pat. No. 5,628,097.

FIELD OF INVENTION

The present invention relates to apertured nonwoven webs and a method of making the same. Apertured nonwoven webs are particularly well suited for use in disposable absorbent articles such as diapers, incontinence briefs, training pants, feminine hygiene garments, and the like.

BACKGROUND OF THE INVENTION

Nonwoven webs formed by nonwoven extrusion processes such as, for example, meltblowing processes and spunbonding processes may be manufactured into products and components of products so inexpensively that the products could be viewed as disposable after only one or a few uses. Representatives of such products include disposable absorbent articles, such as diapers, incontinence briefs, training pants, feminine hygiene garments, and the like.

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art.

A typical absorbent article includes a liquid pervious topsheet, a liquid impervious backsheet joined to the topsheet, and an absorbent core positioned between the topsheet and the backsheet. Nonwoven webs are often used as the topsheet because they are liquid pervious and provide a skin friendly surface. However, in certain uses nonwoven webs do not function all that well as a topsheet as body exudates sometimes hang-up or get caught in the nonwoven web and thus, become trapped against the wearer's skin. One solution to the aforementioned problem is to provide apertures in the nonwoven web so that body exudates may readily penetrate through the nonwoven web and into the underlying absorbent core. Unfortunately, certain techniques used to form apertured nonwoven webs are either costly, create an undesirable harsh feeling against the wearer's skin, or are subject to tearing, particularly when the apertured nonwoven web is to be used as a topsheet on a disposable absorbent article.

As used herein, the term "nonwoven web", refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

As used herein, the term "polymer" generally includes, but is not limited to, hompolymers, copolymers, such as, for example, block, graft, random and alternating copolymers, terpolymers, etc., and blends and modifications thereof Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50 percent without experiencing catastrophic failure.

As used herein, the term "melt-stabilized" refers to portions of a nonwoven web which have been subjected to localized heating and/or localized pressure to substantially consolidate the fibers of the nonwoven web into a stabilized film-like form.

SUMMARY OF THE INVENTION

In accordance with the present invention there is provided a method for selectively aperturing a nonwoven web comprising the steps of:

providing a nonwoven web;

weakening the nonwoven web at a plurality of locations to create a plurality of weakened, melt-stabilized locations; and applying a tensioning force to the nonwoven web to cause the nonwoven web to rupture at the plurality of weakened, melt-stabilized locations creating a plurality of apertures in the nonwoven web coincident with said weakened, melt-stabilized locations.

The nonwoven web may include bonded carded webs, spunbonded webs, or meltblown webs. The meltblown web may include meltblown microfibers. The nonwoven web may also have multiple layers such as, for example, multiple spunbonded layers and/or multiple meltblown layers. The nonwoven material may be made of polymers such as, for example, polyolefins. Exemplary polyolefins include polypropylene, polyethylene, ethylene copolymers and propylene copolymers. The nonwoven web may be an elastic nonwoven web, a nonelastic nonwoven web or an extensible nonwoven web.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, and the like.

Figure 1:
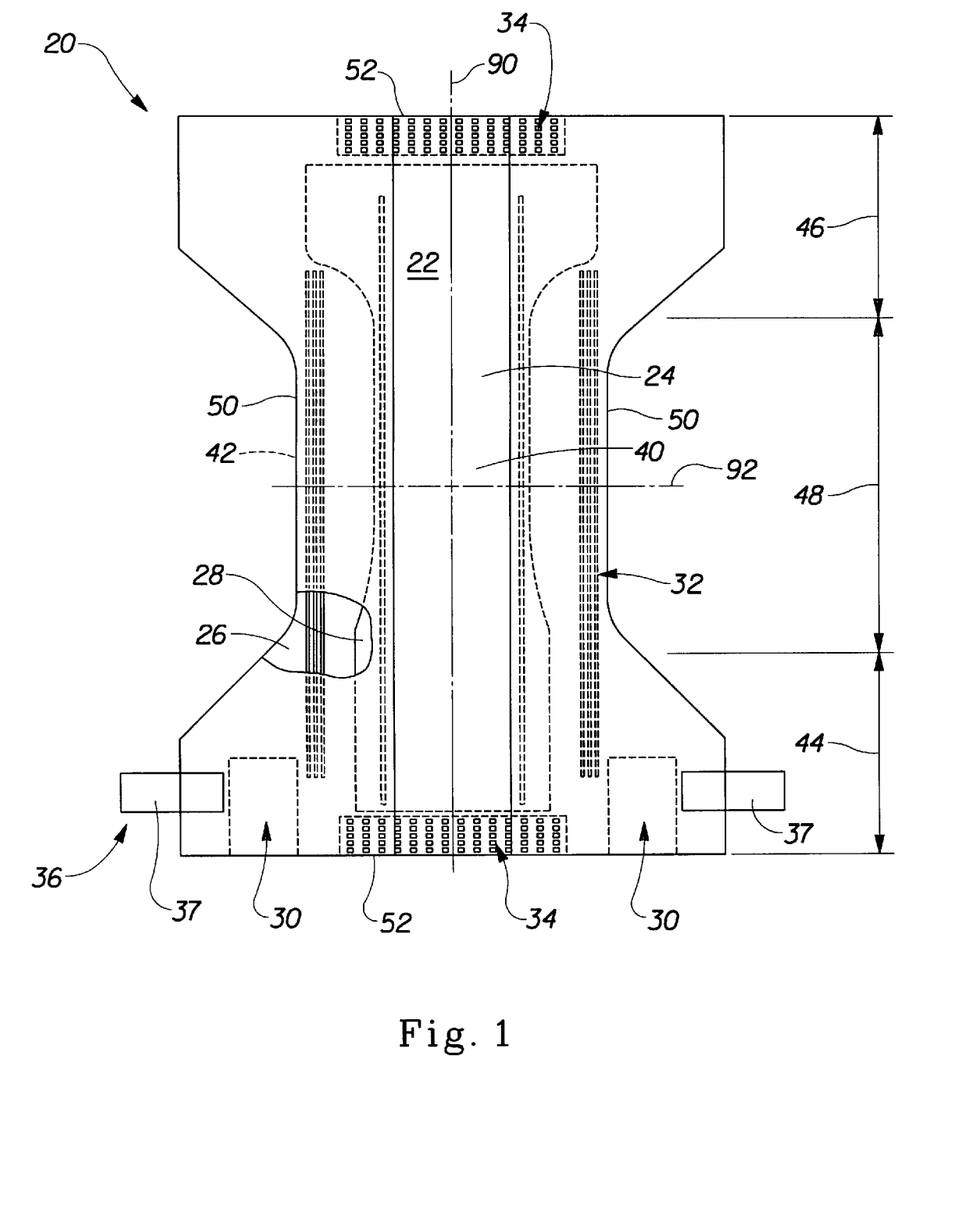
FIG. 1 is a plan view of a disposable diaper embodiment of the present invention having portions cut away to reveal underlying structure, the inner surface of the diaper is facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The diaper preferably further comprises elasticized side panels 30; elasticized leg cuffs 32; elasticized waistbands 34; and a fastening system 36 preferably comprising a pair of securement members 37 and a landing member, (not shown).

The diaper 20 is shown in FIG. 1 to have an inner surface 40 (facing the viewer in FIG. 1), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 90 and a transverse centerline 92. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 comprises at least topsheet 24, backsheet 26 and absorbent core 28. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side, a body-facing side, a pair of side edges, and a pair of waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 is positioned adjacent the garment-facing surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art. Embodiments of the present invention are also contemplated wherein the absorbent core is not joined to the backsheet 26, the topsheet 24, or both in order to provide greater extensibility in the front waist region 46 and the rear waist region 44.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments, however, the backsheet 26 may permit vapors to escape from the absorbent core 28 (i.e., is breathable). Thus, the backsheet 26 preferably comprises a polymeric film such as thermoplastic films of polyethylene or polypropylene. A suitable material for the backsheet 26 is a thermoplastic film having a thickness of from about 0.012 mm (0.5 mil) to about 0.051 mm (2.0 mils).

The topsheet 24 is positioned adjacent the body-facing surface of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 is manufactured from a nonwoven web of synthetic fibers (e.g., polyester, polyethylene, or polypropylene fibers or bicomponent fibers). Other suitable fibers include natural fibers such as wood, cotton, or rayon, or combinations of natural and synthetic fibers.

Figure 2:
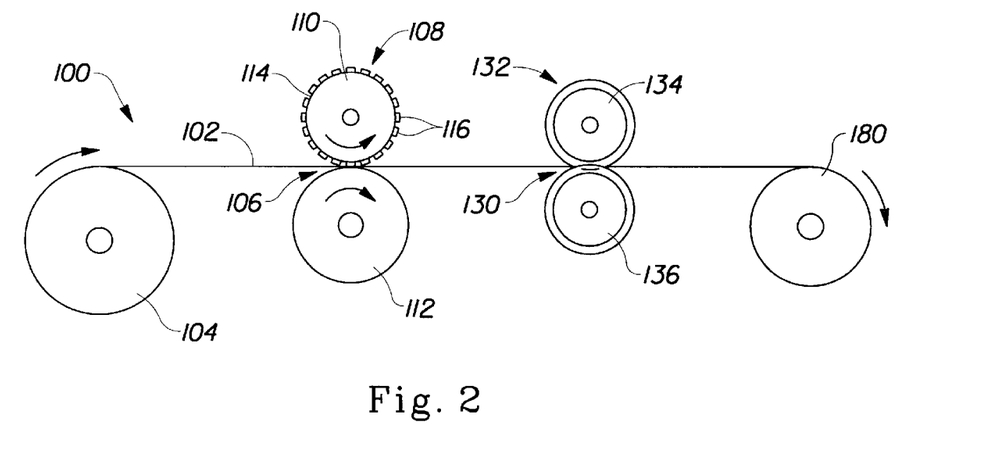
FIG. 2 is a schematic representation of an exemplary process for selectively aperturing a nonwoven web of the present invention.

The topsheet 24 of the present invention preferably comprises an apertured nonwoven web. Referring to FIG. 2 there is schematically illustrated at 100 a process for selectively aperturing a nonwoven web suitable for use as a topsheet on a disposable absorbent article.

According to the present invention, a nonwoven web 102 is unwound from a supply roll 104 and travels in a direction indicated by the arrows associated therewith as the supply roll 104 rotates in the direction indicated by the arrows associated therewith. The nonwoven material 102 passes through a nip 106 of the web weakening roller arrangement 108 formed by rollers 110 and 112.

The nonwoven material 102 may be formed by known nonwoven extrusion processes, such as, for example, known meltblowing processes or known spunbonding processes, and passed directly through the nip 106 without first being bonded and/or stored on a supply roll.

The nonwoven web 102 may be extensible, elastic, or nonelastic. The nonwoven web 102 may be a spunbonded web, a meltblown web, or a bonded carded web. If the nonwoven web is a web of meltblown fibers, it may include meltblown microfibers. The nonwoven web 102 may be made of fiber forming polymers such as, for example, polyolefins. Exemplary polyolefins include one or more of polypropylene, polyethylene, ethylene copolymers, propylene copolymers, and butene copolymers.

In another embodiment, the nonwoven web 102 may be a multilayer material having, for example, at least one layer of a spunbonded web joined to at least one layer of a meltblown web, a bonded carded web, or other suitable material. For example, the nonwoven web 102 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven web may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The nonwoven web 102 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled comingling of fibers and other materials, e.g., wood pulp, staple fibers and particles occurs prior to collection of the fibers.

The nonwoven web of fibers should be joined by bonding to form a coherent web structure. Suitable bonding techniques include, but are not limited to, chemical bonding, thermobonding, such as point calendering, hydroentangling, and needling.

Figure 7:
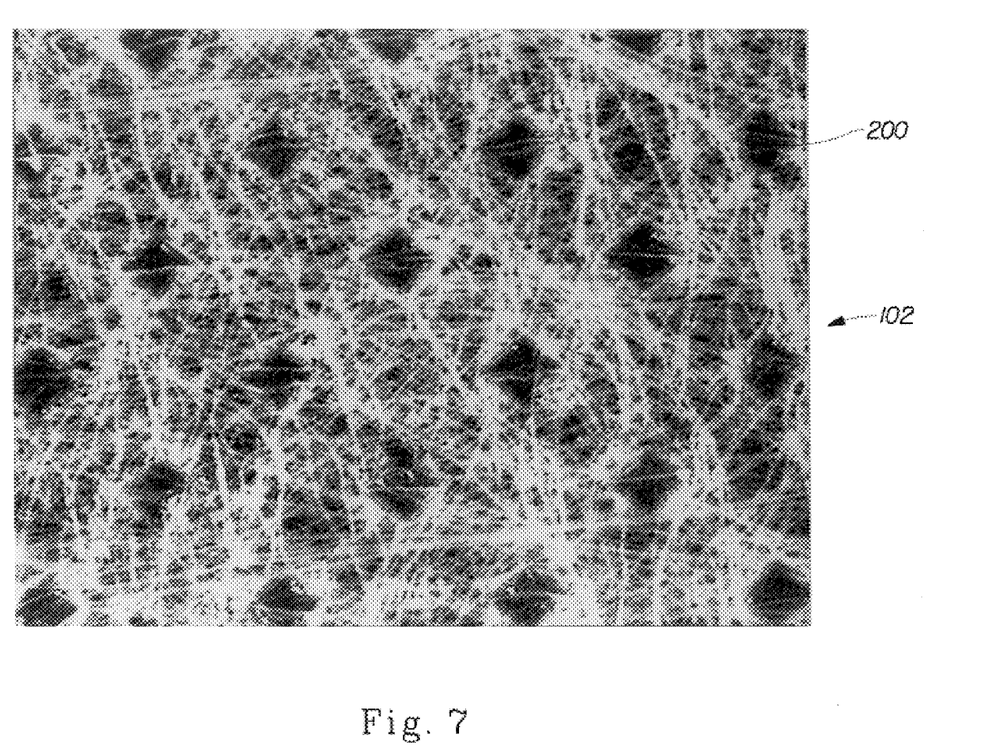
FIG. 7 is an enlarged plan view photograph of a nonwoven web prior to being weakened.

Referring now to FIG. 7 there is shown a photograph of a coherent nonwoven web 102 prior to entering nip 106. As can be seen in FIG. 7 the coherent nonwoven web comprises a plurality of fibers joined together by point calendered bonds 200 to form a coherent web structure.

Figure 3:
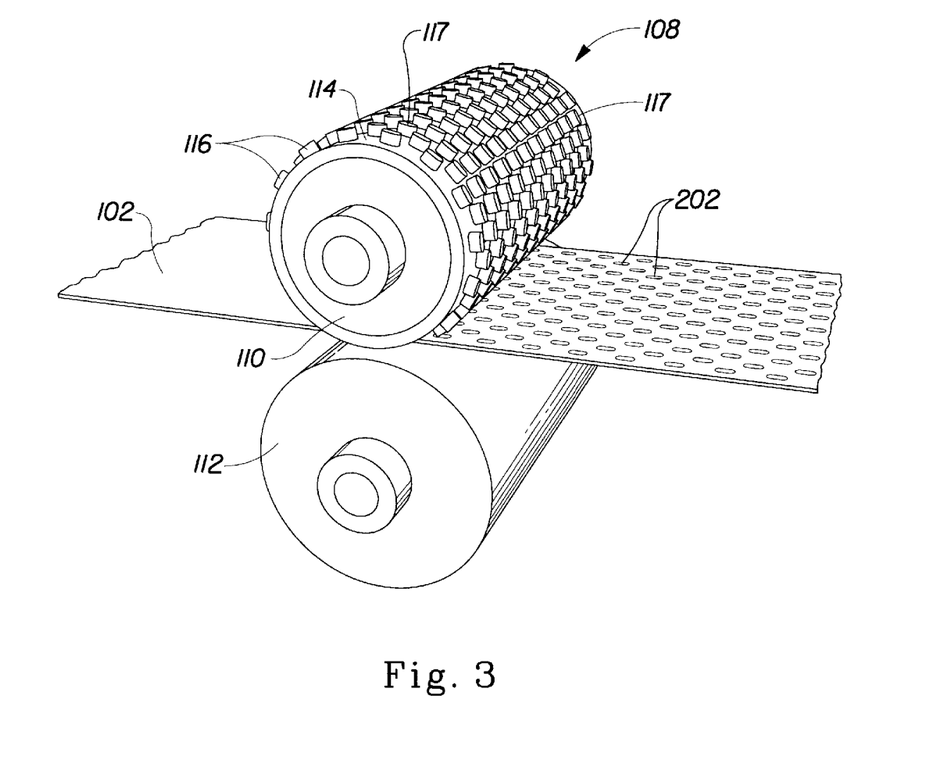
FIG. 3 is an enlarged perspective illustration of a web weakening arrangement of the present invention.

Referring to FIGS. 2 and 3, the nonwoven web weakening roller arrangement 108 preferably comprises a patterned calendar roller 110 and a smooth anvil roller 112. One or both of the patterned calendar roller 110 and the smooth anvil roller 112 may be heated and the pressure between the two rollers may be adjusted by well known means to provide the desired temperature, if any, and pressure to concurrently weaken and melt-stabilize the nonwoven web 102 at a plurality of locations.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to precipitate a weakened, melt-stabilized location in the nonwoven web 102 to effect a predetermined pattern of weakened, melt-stabilized locations in the nonwoven web 102. As shown in FIG. 3, patterned calendar roller 110 has a repeating pattern of protuberances 116 which extend about the entire circumference of surface 114. Alternatively, the protuberances 116 may extend around a portion, or portions of the circumference of surface 114.

The protuberances 116 are preferably truncated conical shapes which extend radially outwardly from surface 114 and which have elliptical distal end surfaces 117. Although it is not intended to thereby limit the scope of the present invention to protuberances of only this configuration. Other suitable shapes for distal ends 117 include, but are not limited to circular, square, rectangular, etc. The roller 110 is finished so that all of the end surfaces 117 lie in an imaginary right circular cylinder which is coaxial with respect to the axis of rotation of roller 110.

The protuberances 116 are disposed in a regular predetermined pattern of rows and columns in the embodiment shown in FIG. 3, although it is not intended to thereby limit the scope of the present invention to the pattern of protuberances of only this configuration. The protuberances may be disposed in any predetermined pattern about patterned calendar roll 110.

Anvil roller 112, is preferably a smooth surfaced, right circular cylinder of steel.

Figure 8:
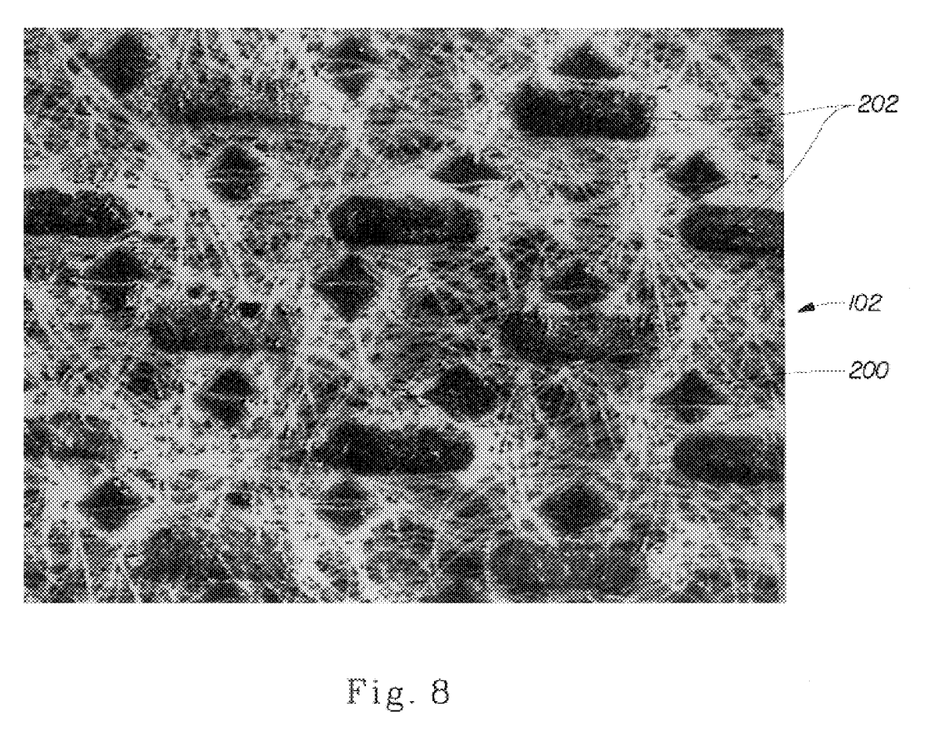
FIG. 8 is an enlarged plan view photograph of a nonwoven web of the present invention after the nonwoven web has been weakened at a plurality of locations.

FIG. 8 is a photograph of the nonwoven web 102 after having passed through the weakening roller arrangement 108, and prior to passing through the nip 130 of the incremental stretching system 132. As can be seen in the photograph, the nonwoven web 102 includes a plurality of weakened, melt-stabilized locations 202. Weakened, melt-stabilized locations 202 generally correspond to the pattern of protuberances 116 extending from the surface 114 of patterned calendar roller 110. As seen in FIG. 8, the nonwoven web 102 also includes coherent web forming point calendered bonds 200 which serve to maintain the structural integrity of the nonwoven web 102.

From the weakening roller arrangement 108, the nonwoven web 102 passes through nip 130 formed by the incremental stretching system 132 employing opposed pressure applicators having three-dimensional surfaces which at least to a degree are complementary to one another.

Figure 4:
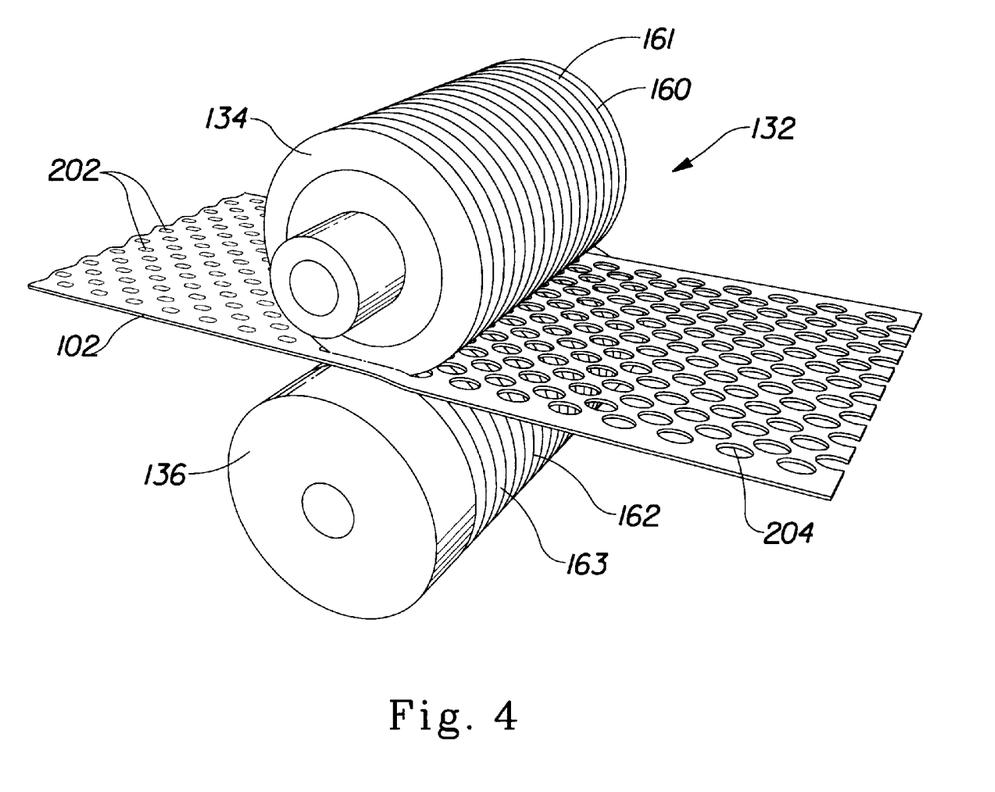
FIG. 4 is an enlarged perspective illustration of an incremental stretching system of the present invention.

Referring now to FIG. 4, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. As the nonwoven web 102 having weakened, melt-stabilized locations 202 passes through the incremental stretching system 132 the nonwoven web 102 is subjected to tensioning in the CD or cross-machine direction causing the nonwoven web 102 to be extended in the CD direction. Alternatively, or additionally the nonwoven web 102 may be tensioned in the MD or machine direction. The tensioning force placed on the nonwoven web 102 is adjusted such that it causes the weakened, melt-stabilized locations 202 to rupture creating a plurality of apertures 204 coincident with the weakened melt-stabilized locations 202 in the nonwoven web 102. However, the bonds of the nonwoven web 102 are preferably strong enough such that they do not rupture during tensioning, thereby maintaining the nonwoven web in a coherent condition even as the weakened, melt-stabilized locations rupture. However, it may be desirable to have some of the bonds rupture during tensioning.

Figure 9:
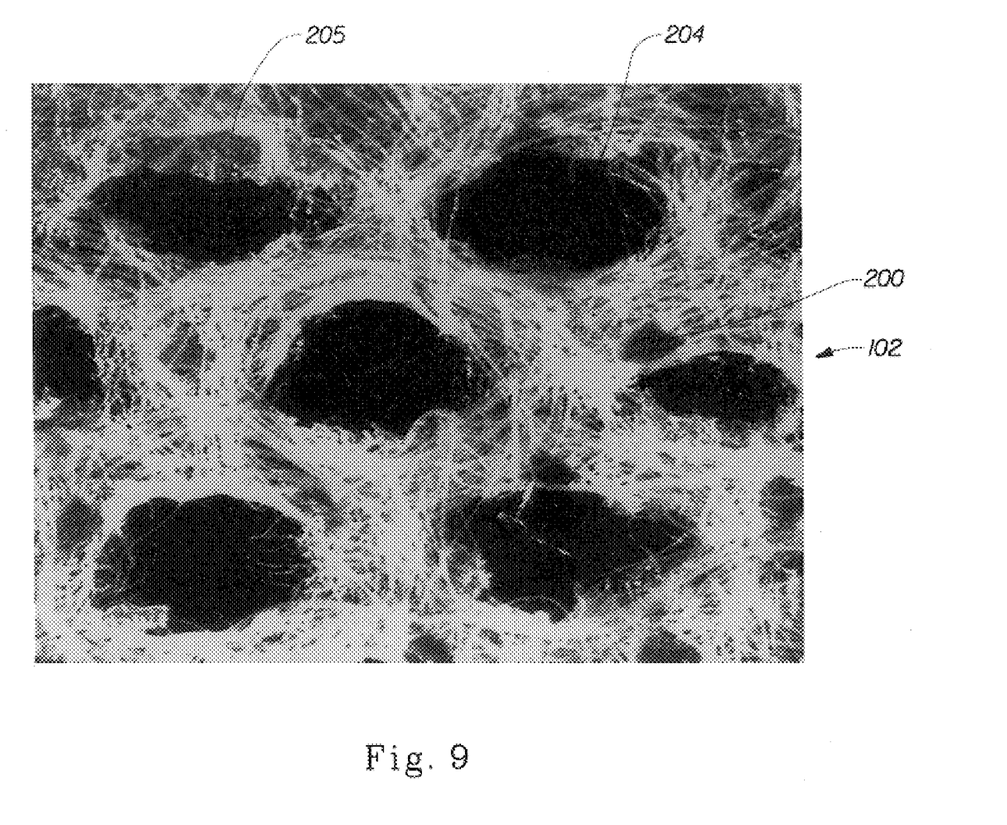
FIG. 9 is an enlarged plan view photograph of a nonwoven web of the present invention after tension has been applied to rupture the nonwoven web at the weakened locations to create apertures in the nonwoven.

Referring now to FIG. 9 there is shown a photograph of the nonwoven web 102 after having been subjected to the tensioning force applied by the incremental stretching system 132. As can be seen in the photograph, the nonwoven web 102 now includes a plurality of apertures 204 which are coincident with the weakened, melt-stabilized locations 202 of the nonwoven web shown in FIG. 8. A portion of the circumferential edges of apertures 204 include remnants 205 of the meltstabilized locations 202. It is believed that the remnants 205 help to resist further tearing of the nonwoven web particularly when the nonwoven web is used as a topsheet on a disposable absorbent article.

Other exemplary structures of incremental stretching mechanisms suitable for incrementally stretching or tensioning the nonwoven web are described in International Pat. Publication No. WO 95/03765, published Feb. 9, 1995, in the name of Chappell, et al., the disclosure of which is incorporated herein by reference.

The selectively apertured nonwoven web may also be used as a topsheet on other disposable absorbent articles such as for example, incontinence briefs, training pants, feminine hygiene garments and the like. The selectively apertured nonwoven web may also be used in other portions of a disposable absorbent article such as, for example, as an acquisition layer positioned between the topsheet and the absorbent core, as part of the absorbent core, or as portions of other components of the disposable absorbent article.

The nonwoven web 102 is preferably taken up on wind-up roll 180 and stored. Alternatively, the nonwoven web 102 may be fed directly to a production line where it is used to form a topsheet on a disposable absorbent article.

Figure 5:
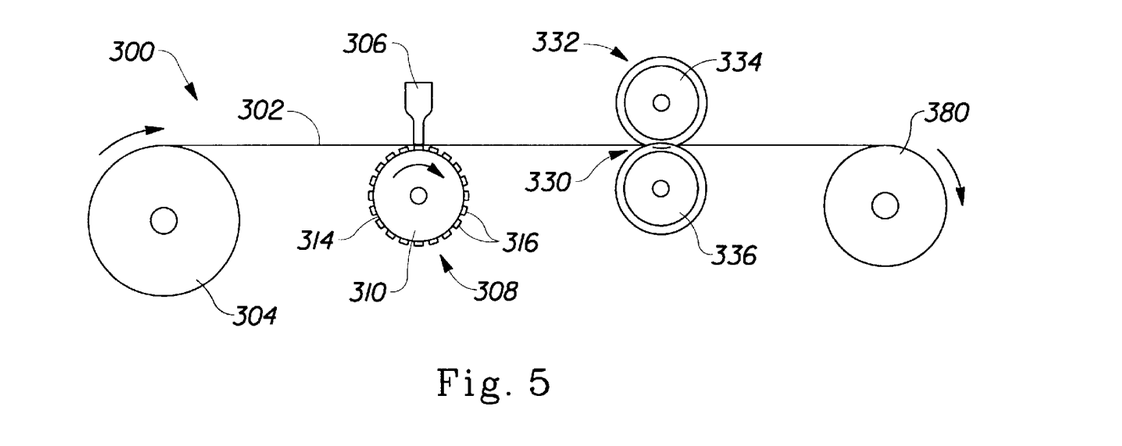
FIG. 5 is a schematic representation of another process for selectively aperturing a nonwoven web of the present invention.

Referring to FIG. 5 there is schematically illustrated at 300 another process for selectively aperturing a nonwoven web of the present invention. A nonwoven web 302 is unwound from a supply roll 304 and travels in a direction indicated by the arrows associated therewith as the supply roll 304 rotates in the direction indicated by the arrows associated therewith. The nonwoven material 302 is forwarded through the web weakening arrangement 308.

The nonwoven material 302 may be formed by known extrusion processes, such as, for example, known melt-blowing processes or known spunbonding processes, and passed directly through the web weakening arrangement 308.

The nonwoven web 302 may be extensible, elastic or non-elastic. The nonwoven web 302 may be a spunbonded web, a meltblown web, or a bonded carded web. If the nonwoven web is a web of meltblown fibers, it may include meltblown microfibers. The nonwoven web 302 may be made of fiber forming polymers such as, for example, polyolefins. Exemplary polyolefins include one or more of polypropylene, polyethylene, ethylene copolymers, propylene copolymers, and butene copolymers.

In another embodiment, the nonwoven web 302 may be a multilayer material having, for example, at least one layer of a spunbonded web joined to at least one layer of a meltblown web, a bonded carded web, or other suitable material.

The nonwoven web may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The nonwoven web 302 may also be a composite made up of a mixture of two or more different fibers or a mixture of fibers and particles. Such mixtures may be formed by adding fibers and/or particles to the gas stream in which the meltblown fibers or spunbond fibers are carried so that an intimate entangled co-mingling of fibers and other materials, e.g., wood pulp, staple fibers and particles occurs prior to collection of the fibers.

The nonwoven web of fibers should be joined by bonding to form a coherent web structure. Suitable bonding techniques, include, but are not limited to, chemical bonding, thermobonding, such as point calendering, hydroentangling, and needling.

Figure 6:
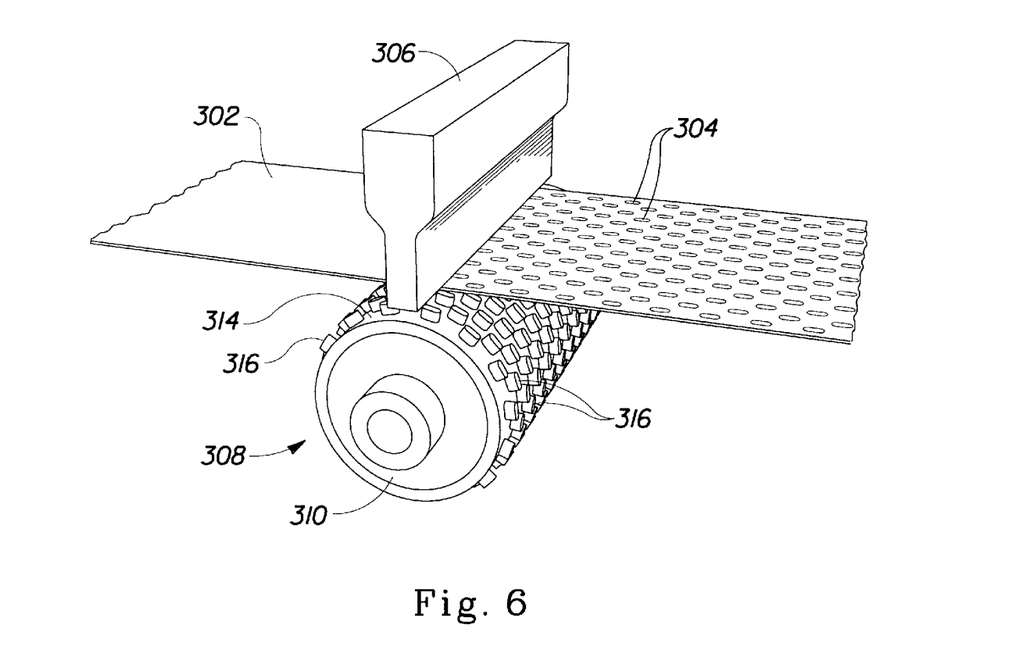
FIG. 6 is an enlarged perspective illustration of another web weakening arrangement of the present invention.

Referring to FIGS. 5 and 6, the nonwoven web weakening arrangement 308 preferably comprises an ultrasonic transducer 306 and a cylinder 310. As the nonwoven material 302 is forwarded between the ultrasonic transducer 306 and the anvil cylinder 310, the nonwoven web 302 is subjected to ultrasonic vibrational energy whereupon predetermined pattern locations of the nonwoven web 302 are weakened and melt-stabilized. Anvil 310 has a multiplicity of discrete pattern protuberances which are generally designated 316 disposed on its outwardly facing surface 314 in a predetermined pattern which extends about the entire circumference of the anvil cylinder. The protuberances 316 are disposed in a predetermined pattern with each protuberance 316 being configured and disposed to precipitate a weakened, melt-stabilized location 304 in the nonwoven web 302 to effect a predetermined pattern of weakened, melt-stabilized locations in the nonwoven web 302. As shown in FIG. 6, anvil 310 has a repeating pattern of protuberances 316 which extend about the entire circumference of surface 314. Alternatively, the protuberances 316 may extend around a portion, or portions of the circumference of surface 314.

The protuberances 316 are preferably truncated conical shapes which extend radially outward from the surface 314 and which have elliptical distal end surfaces. Other suitable shapes for the distal end include, but are not limited to, circular, square, rectangular, etc. The anvil 310 is finished so that all of the end surfaces lie in an imaginary right circular cylinder which is coaxial with respect to the axis of rotation of anvil 310.

After having passed through the weakening arrangement 308, and prior to passing through the nip 330 of the incremental stretching system 332, the nonwoven web 302 includes a plurality of weakened, melt-stabilized locations 304 which generally correspond to the pattern of protuberances 316 extending from the surface 314 of anvil 310.

From the weakening arrangement 308, the nonwoven web 102 passes through nip 330 formed by the incremental stretching system 332 employing opposed pressure applicators having three-dimensional surfaces which at least to a degree are complementary to one another. The incremental stretching system 332 preferably comprises incremental stretching rollers 334 and 336. The incremental stretching roller 334 includes a plurality of teeth and corresponding grooves which extend about the entire circumference of the roller 334. Incremental stretching roller 336 includes a plurality of teeth and a plurality of corresponding grooves. Teeth on roller 334 intermesh or engage with the grooves on roller 136, while the teeth on roller 336 intermesh with or engage with the grooves on the roller 334. As the nonwoven web 302 having weakened, melt-stabilized locations 304 passes through the incremental stretching system 332, the nonwoven web is subjected to tensioning causing the web to be extended. The tensioning force placed on the nonwoven web is adjusted such that it causes the weakened, melt-stabilized locations 304 to rupture creating a plurality of apertures in the nonwoven web which are coincident with the weakened melt-stabilized locations.

The nonwoven web 302 is preferably taken up on wind-up roll 380 and stored. Alternatively, the nonwoven web 302 may be fed directly to a production line where it is used to form a topsheet on a disposable absorbent article.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff comprising a barrier flap and a spacing element such as described in the above-referenced U.S. Pat. No. 4,909,803. In a preferred embodiment, the elasticized leg cuff 32 additionally comprises an elastic gasketing cuff with one or more elastic strands, positioned outboard of the barrier cuff such as described in the above-referred U.S. Pat. No. 4,695,278.

The diaper 20 preferably further comprises an elasticized waistband 34 that provides improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges of the absorbent core 28 and generally forms at least a portion of the end edge of the diaper 20. Disposable diapers are generally constructed so as to have two elasticized waistbands, one positioned in the rear waist region and one positioned in the front waist region, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. The elasticized waistband 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell; each of these references being incorporated herein by reference.

In a preferred embodiment, the diaper 20 also comprises elasticized side panels 30 disposed in the rear waist region 44. (As used herein, the term "disposed" is used to mean that an element(s) of the diaper is formed joined and positioned) in a particular place or position as a unitary structure with other elements of the diaper or as a separate element joined to another element of the diaper.) The elasticized side panels 30 provide an elastically extensible feature that provides a more comfortable and contouring fit by initially conformably fitting the diaper to the wearer and sustaining this fit throughout the time of wear well passed when the diaper has been loaded with exudates since the elasticized side panels allow the sides of the diaper to expand and contract. The elasticized side panels 30 further provide more effective application of the diaper 20 since even if the diaperer pulls one elasticized side panel 30 farther than the other during the application (asymmetrically), the diaper 20 will "self-adjust" during wear. While the diaper 20 of the present invention preferably has the elasticized side panels 30 disposed in the rear waist region 44; alternatively, the diaper 20 may also be provided with elasticized side panels disposed in the front waist region 46 and the rear waist region 44. While the elasticized side panels 30 may be constructed in a number of configurations, examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992; each of which are incorporated herein by reference. Suitable elastic materials for use as the elasticized side panels include elastomeric foams, synthetic or natural rubber, synthetic or natural rubber foams, elastomeric films, elastomeric scrim, elastomeric woven or nonwoven webs, elastomeric composites such as elastomeric nonwoven laminates, or the like.

The diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. Exemplary fastening systems are disclosed in U.S. Pat. No. 4,869,724 issued to Scripps on Sep. 26, 1989; U.S.

Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; U.S. Pat. No. 3,848,594 issued to Buell on Nov. 19, 1974; and U.S. Pat. No. 4,662,875 issued to Hirotsu and Robertson on May 5, 1987. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web made according to the method comprising the steps of:
    a) providing a nonwoven web, wherein said nonwoven web is provided with a patterned plurality of spaced apart discrete bonds to form a coherent web structure;
    b) weakening said nonwoven web at a plurality of locations to create a plurality of weakened, melt-stabilized locations, wherein a portion of said spaced apart descrete bonds are seperated from said melt-stabilized locations; and
    c) applying a tensioning force to said nonwoven web to cause said nonwoven web to rupture at said plurality of weakened, melt-stabilized locations so as to create a plurality of apertures in said nonwoven web coincident with said plurality of weakened, melt-stabilized locations, said apertures having a circumferential edge, a portion of which edge is defined by a remnant of the melt stabilized locations, without substantially rupturing any of said spaced apart discrete seperated bonds that are from said melt stabilized locations.

2. A fibrous nonwoven web comprising a plurality of apertures formed by application of a tensioning force, said apertures coincident with a plurality of weakened, melt-stabilized locations, said apertures having a circumferential edge, a portion of said circumferential edge being defined by a remnant of said melt-stabilized locations and further comprising a patterned plurality of spaced apart discrete bonds, wherein said spaced apart discrete bonds are seperated from said melt stabilized locations, and further wherein said fibers are joined by said spaced apart discrete bonds to form a coherent web structure, said spaced apart discrete bonds being substantially unruptured by said application of said tensioning force.

3. The nonwoven web of claim 2, wherein said nonwoven web forms a topsheet on a disposable absorbent article.

4. The nonwoven web of claim 3, wherein said nonwoven web forms a topsheet on a disposable diaper.

5. The nonwoven web of claim 3, wherein said nonwoven web forms a topsheet on a feminine hygiene garment.

6. The nonwoven web of claim 2 wherein said nonwoven web is a web selected from the group consisting of a bonded carded web of fibers, a web of spunbonded fibers, a web of meltblown fibers, and a multilayer material including at least one of said webs.

7. The nonwoven web of claim 6 wherein said meltblown web includes meltblown microfibers.

8. The nonwoven web of claim 6 wherein said fibers comprise a polymer selected from the group consisting of polyolefins, polyesters, and polyamides.

9. The nonwoven web of claim 8 wherein said polyolefin is selected from the group consisting of one or more of polyethylene, polypropylene, polybutene, ethylene copolymers, propylene copolymers, and butene copolymers.

10. The nonwoven web of claim 9 wherein said nonwoven web is a composite material comprising a mixture of said fibers and one or more other materials selected from the group consisting of wood pulp, staple fibers, particulates and superabsorbent materials.

11. The nonwoven web of claim 2 wherein said nonwoven web comprises an elastic nonwoven web.

12. The nonwoven web of claim 2 wherein said nonwoven web comprises a nonelastic nonwoven web.

13. The nonwoven web of claim 2 wherein said nonwoven web comprises an extensible nonwoven web.

* * * * *